(12) United States Patent
Friedlander et al.

(10) Patent No.: US 8,566,113 B2
(45) Date of Patent: Oct. 22, 2013

(54) METHODS, SYSTEMS AND COMPUTER PROGRAM PRODUCTS FOR PROVIDING A LEVEL OF ANONYMITY TO PATIENT RECORDS/INFORMATION

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 2638 days.

(21) Appl. No.: 11/349,408

(22) Filed: Feb. 7, 2006

(65) Prior Publication Data

US 2007/0185737 A1    Aug. 9, 2007

(51) Int. Cl.
  *G06Q 10/00*    (2012.01)
(52) U.S. Cl.
  USPC ............ 705/2; 705/3; 705/51; 726/4; 726/17; 713/193; 710/1; 600/300; 380/282; 380/277
(58) Field of Classification Search
  USPC ....... 726/4, 17; 705/2, 3, 51; 713/193; 710/1; 707/103 R; 600/300; 380/282, 277
  See application file for complete search history.

(56) References Cited

U.S. PATENT DOCUMENTS

| | | | |
|---|---|---|---|
| 4,328,978 A | | 5/1982 | McLaughlin |
| 5,881,225 A | * | 3/1999 | Worth .............................. 726/17 |
| 5,911,143 A | * | 6/1999 | Deinhart et al. .......... 707/103 R |
| 5,991,758 A | | 11/1999 | Ellard |
| 6,023,765 A | * | 2/2000 | Kuhn ................................ 726/4 |
| 6,024,699 A | | 2/2000 | Surwit et al. |
| 6,058,391 A | | 5/2000 | Gardner |
| 6,189,004 B1 | | 2/2001 | Rassen et al. |
| 6,212,524 B1 | | 4/2001 | Weissman et al. |
| 6,377,993 B1 | | 4/2002 | Brandt et al. |
| 6,385,604 B1 | | 5/2002 | Bakalash et al. |
| 6,397,224 B1 | | 5/2002 | Zubeldia et al. |
| 6,509,898 B2 | | 1/2003 | Chi et al. |
| 6,578,043 B2 | | 6/2003 | Nye |

(Continued)

FOREIGN PATENT DOCUMENTS

| | | |
|---|---|---|
| JP | 2002312373 A | 10/2002 |
| JP | 2002342484 A | 11/2002 |

(Continued)

OTHER PUBLICATIONS

Adam et al., "Positive Patient Identification: a Practical Solution to a Challenging Problem," Toward an Electronic Patient '97. Conference and Exposition. Proceedings, Pt. vol. 3, pp. 100-108, 1997—Abstract Only.

(Continued)

*Primary Examiner* — Dilek B Cobanoglu
(74) *Attorney, Agent, or Firm* — Yudell Isidore Ng Russell PLLC

(57) ABSTRACT

Methods, systems and computer program products are provided for providing a level of anonymity to patient records/information. A unique user identification (ID) associated with a current user is received at an interface of a computer database environment. A first role code associated with a first role of the current user is received at the interface of the computer database environment. The current user is allowed access to a defined set of patient records/information in the computer database environment. The defined set of patient records/information being defined based on the user ID and the first role code of the current user.

30 Claims, 4 Drawing Sheets

(56) References Cited

U.S. PATENT DOCUMENTS

| | | | |
|---|---|---|---|
| 6,629,106 | B1 | 9/2003 | Narayanaswamy et al. |
| 6,636,850 | B2 | 10/2003 | Lepien |
| 6,714,979 | B1 | 3/2004 | Brandt et al. |
| 6,941,271 | B1* | 9/2005 | Soong .............................. 705/3 |
| 6,941,311 | B2 | 9/2005 | Shah et al. |
| 6,978,268 | B2 | 12/2005 | Thomas et al. |
| 6,996,567 | B2 | 2/2006 | Ghukasyan |
| 7,035,849 | B2 | 4/2006 | Tifft |
| 7,080,081 | B2 | 7/2006 | Agarwal et al. |
| 7,107,155 | B2 | 9/2006 | Frudakis |
| 7,111,010 | B2 | 9/2006 | Chen |
| 7,181,017 | B1* | 2/2007 | Nagel et al. ................... 380/282 |
| 7,191,183 | B1 | 3/2007 | Goldstein |
| 7,234,064 | B2* | 6/2007 | Menschik et al. ............. 713/193 |
| 7,362,868 | B2* | 4/2008 | Madoukh et al. ............. 380/277 |
| 2002/0010679 | A1* | 1/2002 | Felsher ............................ 705/51 |
| 2002/0099691 | A1 | 7/2002 | Lore et al. |
| 2002/0156791 | A1 | 10/2002 | Nesamoney et al. |
| 2003/0074222 | A1 | 4/2003 | Rosow et al. |
| 2003/0088438 | A1 | 5/2003 | Maughan et al. |
| 2003/0126148 | A1 | 7/2003 | Gropper et al. |
| 2003/0126156 | A1 | 7/2003 | Stoltenberg et al. |
| 2003/0171876 | A1 | 9/2003 | Markowitz |
| 2003/0191699 | A1 | 10/2003 | Deveault et al. |
| 2004/0064449 | A1 | 4/2004 | Ripley et al. |
| 2004/0111298 | A1 | 6/2004 | Schoenberg |
| 2004/0181526 | A1 | 9/2004 | Burdick et al. |
| 2004/0220836 | A1 | 11/2004 | Doherty et al. |
| 2005/0010442 | A1* | 1/2005 | Kragh .............................. 705/2 |
| 2005/0075544 | A1* | 4/2005 | Shapiro et al. ................. 600/300 |
| 2005/0076158 | A1* | 4/2005 | Kwon .............................. 710/1 |
| 2005/0182722 | A1 | 8/2005 | Meyer et al. |
| 2005/0246189 | A1 | 11/2005 | Monitzer et al. |
| 2006/0041450 | A1 | 2/2006 | Dugan |

FOREIGN PATENT DOCUMENTS

| | | |
|---|---|---|
| WO | WO 96/27163 | 9/1996 |
| WO | WO 01/08077 A1 | 2/2001 |
| WO | WO01/37097 A1 | 5/2001 |

OTHER PUBLICATIONS

Chatfield, "Marketing an HMO by 'Smart' ID Cards with Patient History on an Electronic Medical Record," Proceedings. Toward an Electronic Patient Record '96. Twelfth International Symposium on the Creation of Electronic Health Record System and Global Conference on Patient Cards, Pt. vol. 1, pp. 608-620, 1996—Abstract Only.

Gabrieli, "Guide for Unique Healthcare Identifier Model," *Journal of Clinical Computing*, vol. 21, No. 5, pp. 101-139, 1993—Abstract Only.

Goehring, "Identification of Patients in Medical Databases—Soundex Codes Versus Match Code," *Medical Informatics*, vol. 10, No. 1, pp. 27-34, Jan.-Mar. 1985—Abstract Only.

Goodwin, Linda et al., "Data Mining for Preterm Birth Prediction," Proceedings of the 2000 ACM Symposium on Applied Computing (Mar. 19-21, 2000—Como, Italy), vol. 1, pp. 46-51pp. 46-51.

Grimson et al., "The SI Challenge in Health Care," *Communications of the ACM*, vol. 43, No. 6, Jun. 2000, pp. 49-55.

Hoshiai et al., "SION Architecture: Semantic Information-Oriented Network Architecture," *Transactions of the Institute of Electronics, Information and Communication Engineers B.*, vol. J84-B, No. 3, pp. 411-424, Mar. 2001—Abstract Only.

Kim et al. "A Solution to the Distribution and Standardization of Multimedia Medical Data in E-Health" *ACM International Conference Proceeding Series 147 Proceedings of the Pan-Sydney area workshop on Visual Information processing* 11 161-164 (2001).

Lowery et al., "Barriers to Implementing Simulation in Health Care," Proceedings from the 1994 Winter Simulation Conference, pp. 868-875.

Phillips Jr. et al. "Person-Matching by Electronic Methods" *Communications of the ACM* 5(7):404-407 (1962).

Polak et al., "Using Automated Analysis of the Resting Twelve-Lead ECG to Identify Patients at Risk of Developing Transient Myocardial Ischaemia—an Application of an Adaptive Logic Network," *Physiological Measurement*, vol. 18, No. 4, pp. 317-325, Nov. 1997.

Shelfer et al., "Smart Card Evolution," *Communications of the ACM*, vol. 45, No. 7, Jul. 2002, pp. 83-88.

Wang, C., "A COBRA-based Object Framework with Patient Identification Translation and Dynamic Linking. Methods for Exchanging Patient Data," *Methods of Information in Medicine*, vol. 38, No. 1, pp. 56-65, Mar. 1999—Abstract Only.

Zarowski et al., "Some Algorithms for Circadian Rhythm Identification," 2001 IEEE Pacific Rim Conference on Communications, Computers, and Signal Processing, Pt. vol. 2, pp. 425-428, 2001—Abstract Only.

\* cited by examiner

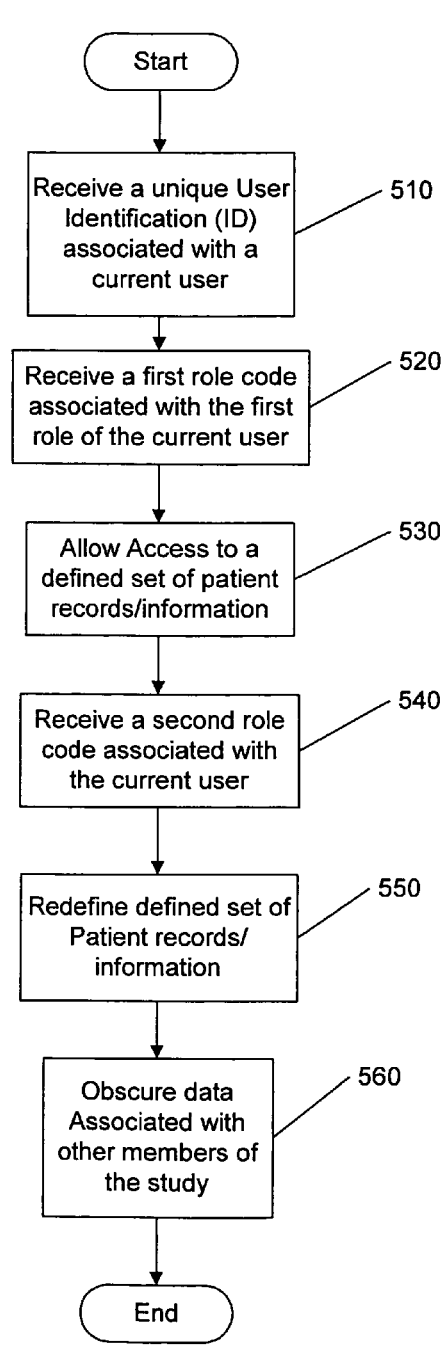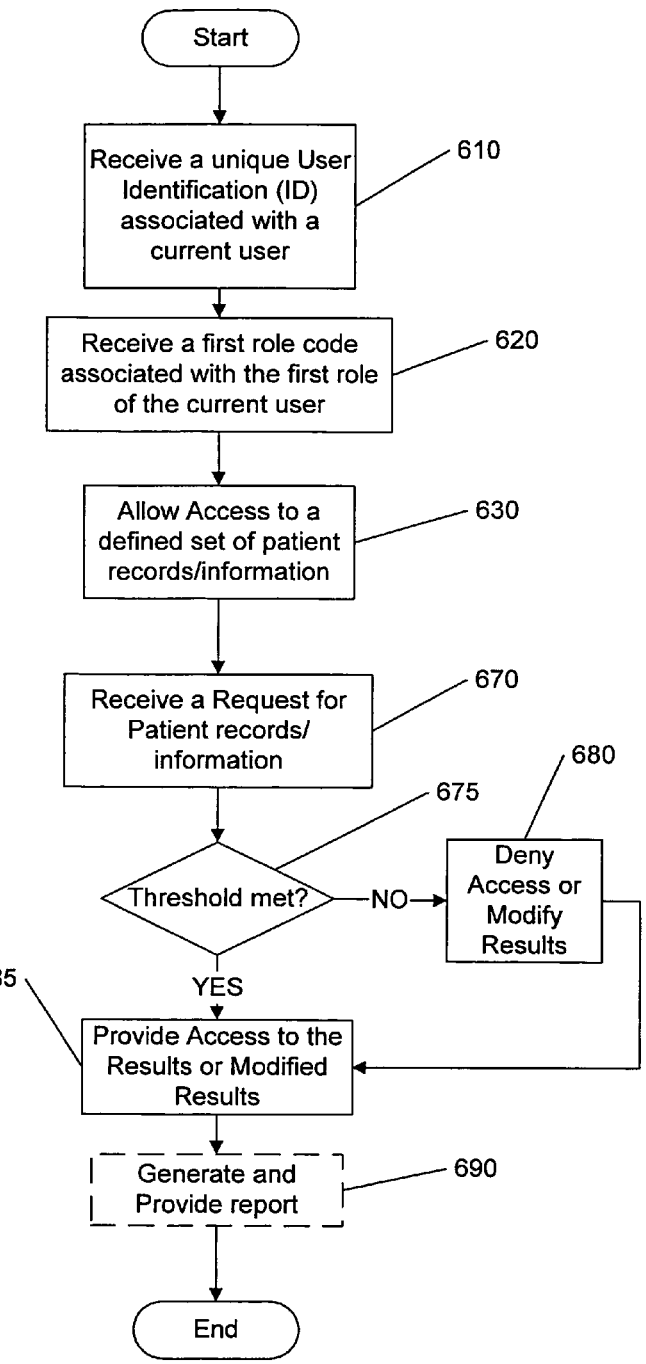
Figure 5                    Figure 6

METHODS, SYSTEMS AND COMPUTER PROGRAM PRODUCTS FOR PROVIDING A LEVEL OF ANONYMITY TO PATIENT RECORDS/INFORMATION

FIELD OF THE INVENTION

The invention relates to data processing in general and, more particularly, to organization of data.

BACKGROUND OF THE INVENTION

Access to patient records/information is highly regulated. Access to this information may be federally regulated, state regulated and/or regulated at the local level, such as by a hospital institutional review board (IRB). However, access to these records may be provided to those people, doctors, nurses and the like, who provide medical treatment. For example, an emergency room doctor may need to access the medical records of an unconscious accident victim who cannot communicate any information to the doctor. Thus, although a patient's privacy is very important, there is a delicate balance between keeping patient records confidential to protect the patient's privacy and providing access to at least portions of patient records for treatment, research and/or medical purposes. Conventional methods of regulating access to patient records can be very complex, over inclusive, under inclusive and/or inflexible.

SUMMARY OF THE INVENTION

Some embodiments of the present invention provide methods, systems and computer program products for providing a level of anonymity to patient records/information. A unique user identification (ID) associated with a current user is received at an interface of a computer database environment. A first role code associated with a first role of the current user is received at the interface of the computer database environment. The current user is allowed access to a defined set of patient records/information in the computer database environment. The defined set of patient records/information being defined based on the user ID and the first role code of the current user.

In further embodiments of the present invention, a second role code associated with a second role of the current user may be received at the interface of the computer database environment. The defined set of patient records/information to which the current user is allowed access may be redefined based on the user ID and the second role code. The first and second roles of the current user may be associated with a single patient. The single patient may be a member of a medical study. Data associated with other members of the medical study may be obscured to provide a level of anonymity to the other members of the study.

In still further embodiments of the present invention, a request for patient records/information in the defined set of patient records/information may be received at the interface of the computer database environment. It may be determined if results of the received request meet a threshold level of anonymity responsive to the received request. The current user may be provided access to the results of the received request if it is determined that the threshold level of anonymity has been met.

In some embodiments of the present invention, access to the results of the received request may be denied if it is determined that the threshold level of anonymity has not been met. In certain embodiments of the present invention, the results of the received request may be modified so that the modified results meet the threshold level of anonymity if it is determined that the threshold level has not been met. Access to the modified results may be provided.

In further embodiments of the present invention, the user may be allowed access to the defined set of patient records/information based at least one access rule defined by at least one state government official, federal government official and/or local institutional official. A report associated with the current user may be generated summarizing patient records/information accessed by the current user. The generated report may be provided to at least one state government official, federal government official and/or local institution official.

BRIEF DESCRIPTION OF THE DRAWINGS

FIGS. 3 through 6 are flowcharts illustrating operations according to various embodiments of the present invention.

DETAILED DESCRIPTION OF EMBODIMENTS OF THE INVENTION

Figure 1:
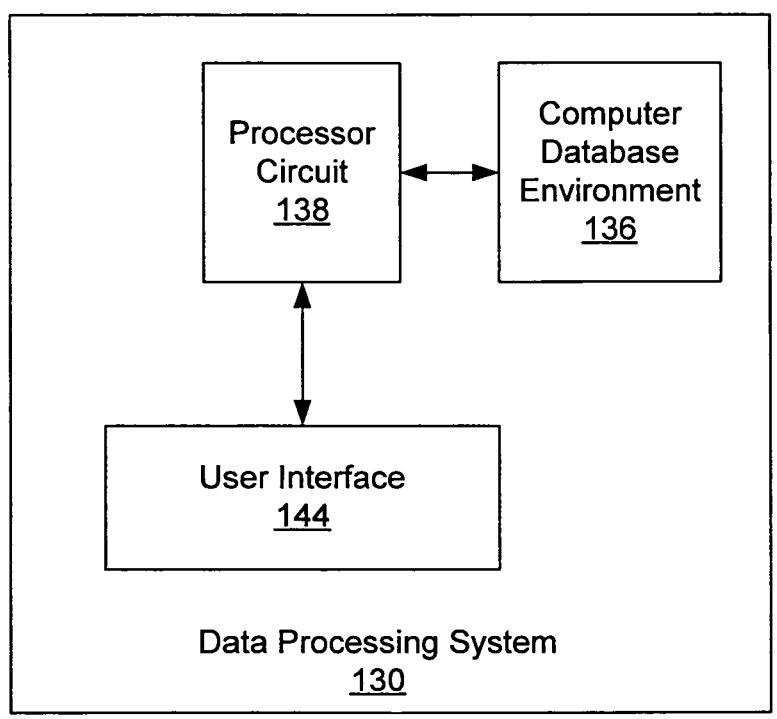
FIG. 1 is a block diagram illustrating systems according to some embodiments of the invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will be appreciated by one of skill in the art, the invention may be embodied as a method, data structure, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems, computer program products and data structures according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to FIGS. 1 through 6. As discussed herein, according to some embodiments of the present invention a level of anonymity may be provided to patient records/information. A computer database environment may be provided. Healthcare related data may be stored in the computer database environment. The healthcare related data may include information about patients, for example, test results, diagnoses, treatments and the like. The healthcare related data may be stored at a single location, for example, in a database on a hospital sever, or may be stored in multiple locations, for example, a doctor's office database, a hospital database, an insurance company database and the like, without departing from the scope of the present invention.

According to some embodiments of the present invention, a current user may provide a unique user identification (ID) associated with the current user at an interface of the computer database environment. Each user, for example, a doctor, nurse, researcher and the like, may be given a unique ID that must be entered each time the user accesses the healthcare related data in the computer database environment. Once the unique ID is entered, the computer database environment may know who the user is, such as a doctor, what the user's security clearance is and any other relevant information about the user. Entering the ID each time healthcare related data is accessed allows a user's actions to be monitored to ensure the user is not accessing information without authorization to do so, which will be discussed further below. The current user also provides a "role code" at the interface of the computer database environment. As used herein, the "role code" identifies the role of the current user at the present time. A set of patient records/information in the computer database environment is defined based on the user ID and the role code of the current user. The current user can only have access to the records/information in the defined set of patient records/information. It will be understood if the user and/or role change, so may the set of patient records/information to which access may be allowed. For example, a nurse-researcher may not have access to the same patient information as a doctor-researcher. Similarly, a physician in a clinical care role may have rights to access to more patient information than the same physician in a researcher role.

It will be further understood that the "role" of the current user may change very quickly. For example, a doctor may be conducting a research study on women in their thirties who have breast cancer. During an examination of one of the members of the study, the doctor may provide his unique ID and a role code indicating that his current role is "research" at an interface of the computer database environment. The doctor's unique ID code together with the research role code defines the set of records/information associated with the member of the research study that may be accessed by the doctor. However, if during the examination, the member of the research study goes into cardiac arrest, the doctors role changes from "researcher" to "medical provider." Thus, the set of patient records/information to which the doctor may be granted access may be redefined based on his unique ID and the medical provider role code.

As will be discussed further below, in some embodiments of the present invention the set of patient records/information may also be defined based on who the patient is. For example, if the patient is a very important public figure, for example, the president of the United States, the set of patient records/information may only be accessed by a limited group of people having the highest security clearance, for example, the president's personal physicians.

Referring now to FIG. 1, a block diagram illustrating systems, for example, data processing system 130, according to some embodiments of the invention will be discussed. In particular, a computer database environment 136 operates under the control of a processor circuit 138. The processor circuit 138 can be a general purpose processor circuit within a general purpose or application specific computer. As described above, the processor circuit 138 may use elements of both hardware and software to carry out the functions described herein.

The system 130 also includes a user interface 144. The user interface device 144 may include, for example, a keyboard or keypad, a display, microphone, speaker and/or other types of input/output functionality that may enable the user to interact with the computer database environment 136 via the processor circuit 138. It will be understood that the elements shown in FIG. 1 may operate on a single computer system or may be distributed among two or more computer systems that operate in cooperation with one another to carry out the operations described herein. The two or more computers may communicate with one another over a network, such as a local area network.

The computer database environment 136 is configured to store healthcare related data. The healthcare related data may be collected from databases, such as databases maintained by doctors' offices, hospitals, insurance companies and the like. Access to the healthcare related data may be regulated at a federal level, state level and/or local level (IRB). Thus, access rules may vary from country to country, state to state and even hospital to hospital. Thus, before accessing the healthcare related data a user enters both his/her unique ID and a role code identifying the user's role at the present time. The set of patient records/information (healthcare related data) the user is allowed access to may be defined based on the user ID and role code. Again, sets of data are defined to comply with the federal (country), state and/or local regulations, i.e., the final set of data to which the user is allowed access must comply with all existing regulations. For example, if a piece of information meets both state and local regulations, but does not meet federal regulations, than this information can not be revealed to the user.

As discussed above, if the user's role changes a second role code may be provided at an interface of the computer database environment 136. The defined set of patient records/information to which the current user is allowed access may be redefined based on the user ID and the second role code.

In some embodiments of the present invention, the patient being examined by the user may be a member of a medical study. The computer database environment may be configured to obscure data associated with other members of the medical study to provide a level of anonymity to the other members of the study. For example, only the patient's name may be displayed and the other members of the study may be identified by numerical IDs, pseudo IDs, and/or multiple IDs so that the user cannot identify the other members without, for example, a key. Thus, embodiments of the present invention not only provide a level of anonymity to the current patient, but to other patients that may be associated with the current patient by way of, for example, being in the same medical study.

At some point, once a user of the computer database environment has entered a unique ID and a role code, he or she may provide a request for patient records/information in the defined set of patient records/information at the interface of the computer database environment. However, just because the records/information is included in the defined set, does not necessarily mean that the user will have access to the information. For example, if displaying the information would allow the user to determine, for example, who that patient(s) is, the information may not be displayed.

The computer database environment 136 may be configured to determine if results of the received request meet a threshold level of anonymity. As used herein, the "threshold level of anonymity" may be based on who the user is, what is the user's current role, how much information is in the set of information to be provided (i.e., how likely is it that this patient will be identified if this information is revealed?), federal, state, local and/or country regulations and the like. For example, the computer database environment 136 may be configured to do a statistical evaluation of the results and determine if the results meet a threshold level of anonymity. If the threshold is met, access to the results of the received request may be provided. If the threshold is not met, access to the results may be denied or modified results may be presented instead.

In some embodiments of the present invention, the computer database environment is configured to look at the prevalence of identification criterion including, for example, the prevalence of the disease state nationally, regionally and at the specific institutions. It may be further configured to handle treatments, such as procedures and medications again based on national, regional and/or institutional prevalence. The assorted portions may be combined by algorithms that determine the level of potential identification that a specific user is permitted to see based on the role of the user, the group to which the user belongs, the group to which the role belongs and the like. In some embodiments of the present invention, the user may be prompted for information that may be used by the algorithms to determine how much information should be revealed to the user. For example, the computer database environment may be configured to check if the user has special IRB authorizations, the reason the information is being requested and the like. If the user is permitted access to all of the records/information requested, the user may be allowed access to all relevant confidential data. If the user is only permitted partial access, the amount of access is determined based on the ID, role code, regulations and the like. The amount and type of information may be determined based on, for example, the demographics of the patient, the disease state of the patient, the treatment, time periods, treating providers and the like. Users may have limited access in the form of deidentified data (data with no names just number IDs), aggregated data (data with respect to multiple patients) and the like.

For example, a user may do a search for all people in a geographic region having a particular type of cancer. If the geographic region is for a very small town, there may only be one person having this type of cancer and revealing it may not meet the threshold level of anonymity because the person would be easily identified. Thus, access to the results may be denied. However, in some embodiments of the present invention, the computer database environment may be configured to provide modified results that meet the threshold level of anonymity if the threshold is not met by the requested results. For example, the computer database environment may be configured to provide results for a larger geographic region so that more than one patient will be present in the results. For example, instead of Raleigh, N.C. the results for the whole state of NC may be provided.

It will be understood that according to some embodiments of the present invention, the computer database environment may be configured to automatically provide modified results when the requested results do not meet the threshold. However, the computer database environment may also be configured to communicate to the user that the results do not meet the threshold level of anonymity and ask questions of the user as to how and if to modify the results.

It will be understood that threshold levels of anonymity may be based on a variety of factors and is not limited to geographic region as discussed above. For example, very specific queries for patients within a very small pool, for example, patients over the age of 80, may produce results that do not meet the threshold level of anonymity. Thus, the computer database environment may be configured to broaden the query so as to broaden the results to be displayed. For example, if the results of a specific query only yielded three results, the query may be broadened so that fifteen results may be displayed. Thus, the likelihood that any one patient out of fifteen may be identified may be decreased, i.e. meets a threshold level of anonymity.

In some embodiments of the present invention, in additional to the user ID and role code, the user may be prompted for additional information. For example, the user may be prompted for relevant information set identifiers, such as IRB authorization or study number. This may further customize the set of patient/information a user may have access to. For example, a doctor may only have rights to see certain information in connection with a specific study and with a specific role.

In some embodiments of the present invention, the computer database environment may be configured to monitor a user's access to the computer database environment. For example, each time a user associated with a unique ID logs into the database, the day, time, role, records accesses and the like may be recorded. A report associated with the user may be generated summarizing this information. These reports may be used by, for example, the IRB, to police the system and make sure the privacy of patients is being protected. If one of the reports contains suspicious information, the user associated with the report may be questioned to determine if any wrong doing has occurred.

In certain embodiments of the present invention, healthcare related data may be retrieved using query tools, such as SQL, MicroStrategy, BusinessObject, Cognos and the like. Furthermore, some embodiments of the present invention may be used in combination with existing database software, such as DB2 from International Business Machines, Armonk, N.Y., the assignee of the present application. Other database software that may be used in some embodiments of the present invention includes Oracle from Oracle of Redwood Shores, Calif., SQL Server from Microsoft Corporation of Redmond, Wash. and Sysbase from Sysbase of Dublin, Calif. The exemplary database software provided herein is provided for exemplary purposes only and embodiments of the present invention are not limited to these examples. Methods of collecting and storing data in databases are known to those having skill in the art and, therefore, will not be discussed in detail herein.

Figure 2:
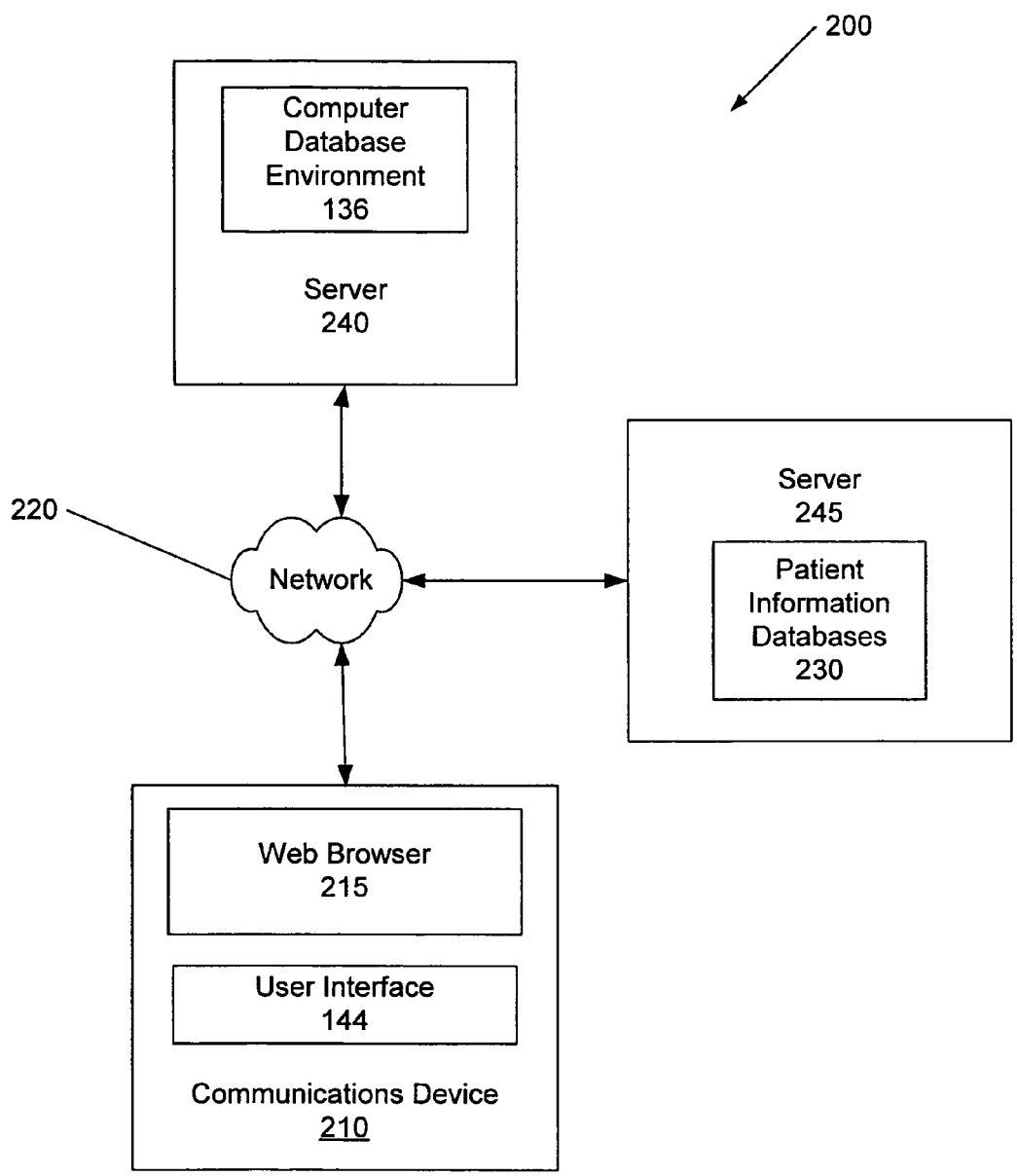
FIG. 2 is a block diagram illustrating some embodiments of the present invention in an exemplary network environment.

An exemplary method of obtaining healthcare related data from a computer database environment while maintaining patient anonymity according to some embodiments of the present invention will now be discussed with respect to FIG. 2. As illustrated, the environment 200 may include a communications device 210, a network 220 and first and second servers 240 and 245. The communications device 210 may be, for example, a laptop computer, a desktop computer, a personal data assistant (PDA), a web capable mobile terminal or any device capable of communicating with the network 220. The communications device 210 may communicate over the network 220, for example, the internet, through a telephone line, a digital subscriber link (DSL), a broadband cable link, a wireless link or the like. The first and second servers 240 and 245 may also communicate over the network 220. Thus, the network 220 may convey data between the communications device 210 and the first and second servers 240 and 245.

As further illustrated, the communications device may include a web browser 215 that may be accessed through the user interface 144. The web browser 215 may allow, for example, a doctor, nurse, researcher or the like, access to a text or graphical interface used to request healthcare related data. For example, the web browser may include a graphical interface that requests the unique ID associated with the user and a role code associated with the user's current role. Once the user enters this information, the user may have access to a set of patient data/information computer database environment 136. The set of data may be defined based on the unique ID, the role code, who the patient is, regulations (federal, state, local and the like) and the like. Thus, the set of data may be defined based on a user's current relationship with the patient, among other things. The computer database environment 136 is configured to statistically analyze the requested data given all the information and present information to the user only if a threshold level of anonymity may be met as discussed above.

It will be understood that although healthcare related data may be stored in the database 136, embodiments of the present invention are not limited to this configuration. For example, a pointer to the information stored in the external databases may be stored in the database 136 instead of storing the information itself. This may allow the database 136 to operate with much less memory associated therewith.

Thus, a user may use the web browser 215 to search and analyze the healthcare related data in the set of patient records/information. As illustrated in FIG. 2, the second server 245 may include patient information databases 230 including, for example, databases maintained hospitals, doctor's offices, insurance companies and the like. Access to the information in the database 136 may be provided while maintaining patient privacy according to some embodiments of the present invention.

Figure 3:
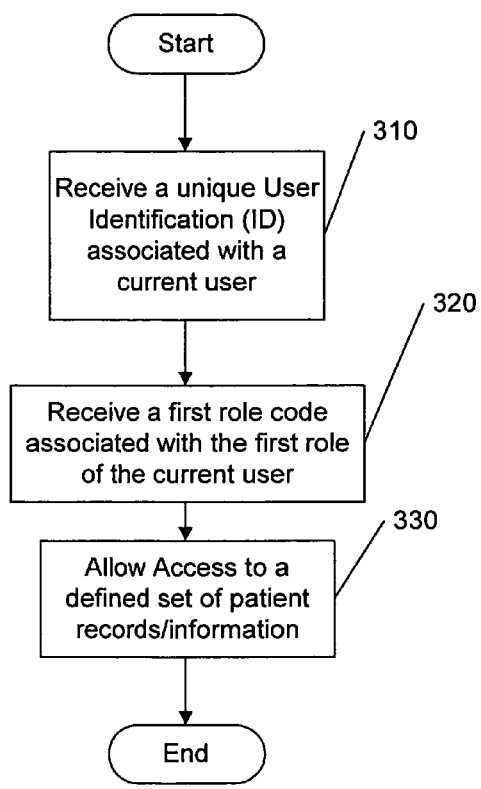

Referring now to FIGS. 3 through 6, flowcharts illustrating operations for providing a level of anonymity to patient records/information according to various embodiments of the present invention will now be discussed. Dotted lines indicate optional steps in the flowcharts. Referring first to FIG. 3, operations begin at block 310 by receiving a unique user identification (ID) associated with a current user at an interface of a computer database environment. As discussed above, each user is assigned a unique ID. When entered, the computer database environment knows who the user is, for example, doctor, nurse, researcher or the like, what the user's security clearance is and the like. A first role code associated with a first role of the current user is also provided at the interface of the computer database environment (block 320). The role code indicates the role of the user at the present time, for example, researcher or medical provider. The user is allowed access to a defined set of patient records/information in the computer database environment (block 330). The defined set of patient records/information is defined based on the unique user ID and the first role code of the current user.

In some embodiments of the present invention, who the patient is and privacy regulations are also used to define the set of patient records/information. For example, if the patient is a public official, access to his or her records may be highly restricted. Furthermore, if one of the federal, state and/or local regulations indicate that certain information should not be revealed, then this information can not be included in the defined set of patient information.

Figure 4:
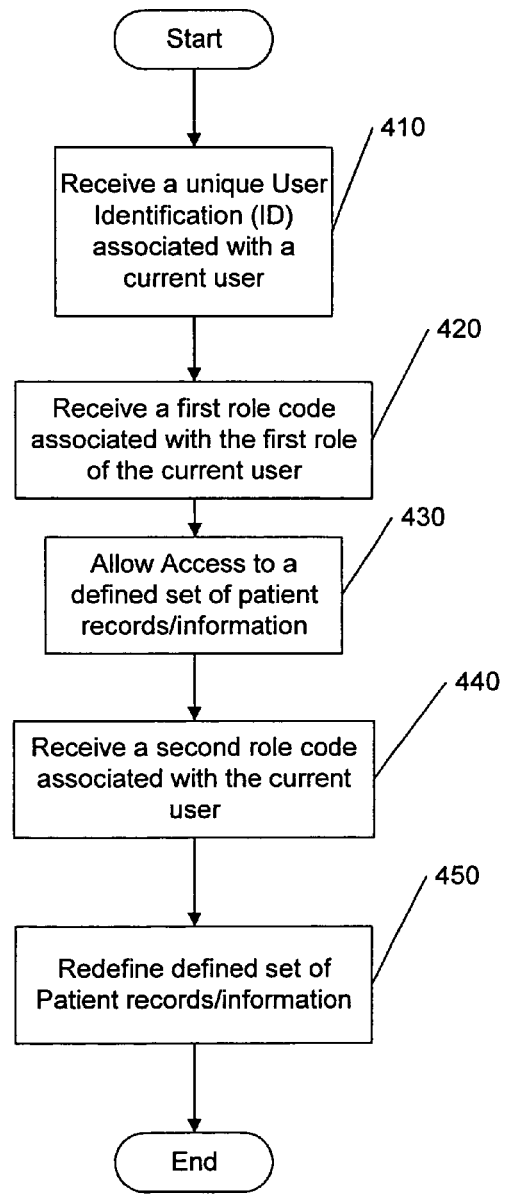

Referring now to the flowchart of FIG. 4, operations begin at block 410 by receiving a unique user identification (ID) associated with a current user at an interface of a computer database environment. A first role code associated with a first role of the current user, for example, researcher, is also provided at the interface of the computer database environment (block 420). The user is allowed access to a defined set of patient records/information in the computer database environment (block 430). The defined set of patient records/information is defined based on the unique user ID and the first role code of the current user. A second role code associated with a second role of the current user, for example, medical provider, is provided at the interface of the computer database environment (block 440). The defined set of patient records/information to which the current user is allowed access may be redefined based on the user ID and the second role code (block 450). For example, a doctor in a "medical provider" role may have access to more information than a doctor in a "researcher" role.

Referring now to FIG. 5, operations begin at block 510 by receiving a unique user identification (ID) associated with a current user at an interface of a computer database environment. A first role code associated with a first role of the current user, for example, researcher, is also provided at the interface of the computer database environment (block 520). The user is allowed access to a defined set of patient records/information in the computer database environment (block 530). The defined set of patient records/information is defined based on the unique user ID and the first role code of the current user. A second role code associated with a second role of the current user, for example, medical provider, is provided at the interface of the computer database environment (block 540). The defined set of patient records/information to which the current user is allowed access may be redefined based on the user ID and the second role code (block 550). In some embodiments of the present invention, the patient is a member of a medical study. Data associated with other members of the medical study may be obscured to provide a level of anonymity to the other members of the study (block 560). For example, information with respect to other members of the study may be provided using pseudo IDs or multiple IDs to obscure their identities.

Referring now to FIG. 6, operations begin at block 610 by receiving a unique user identification (ID) associated with a current user at an interface of a computer database environment. A first role code associated with a first role of the current user, for example, researcher, is also provided at the interface of the computer database environment (block 620). The user is allowed access to a defined set of patient records/information in the computer database environment (block 630). A request is received for patient records/information in the defined set of patient records/information at the interface of the computer database environment (block 670). For example, a request for all the patients over the age of 85 diagnosed with liver cancer in a specific geographic location may be provided. It is determined if the results of this query meet a threshold level of anonymity (block 675). This threshold may be defined based on, for example, federal, local and/or state regulations. If it is determined that the threshold level of anonymity has been met (block 675), access to the results of the received request may be provided (block 685). If, on the other hand, it is determined that the threshold level of anonymity has not been met (block 675), in some embodiments of the present invention, access to the results of the received request may be denied (block 680). In further embodiments of the present invention, if it is determined that the threshold level of anonymity has not been met (block 675), the results of the received request may be modified so that the modified results meet the threshold level of anonymity (block 680) and the modified results may be provided to the user (block 685). For example, if the geographic region is too small and only one person over 85 having liver cancer is included in the results, the geographic region may be made larger or the age limit may be made younger to broaden the results of the query.

Optionally, a report associated with the current user summarizing patient records/information accessed by the current user may be generated and provided to at least one state government official, federal government official and/or local institution official (block 690). These reports may be used to police access to confidential patient information according to some embodiments of the present invention as discussed above.

It will be understood that the circuits and other means supported by each block and combinations of blocks can be implemented by special purpose hardware, software or firmware operating on special or general purpose data processors, or combinations thereof. It should also be noted that, in some alternative implementations, the operations noted in the blocks may occur out of the order noted in the figures. For example, two blocks shown in succession may, in fact, be executed substantially concurrently, or the blocks may sometimes be executed in the reverse order.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A method of providing a level of anonymity to patient records/information, the method comprising:
   receiving a unique user identification (ID) associated with a current user at an interface of a computer database environment;
   receiving a first role code associated with a first role of the current user at the interface of the computer database environment;
   allowing access to a defined set of patient records/information in the computer database environment, wherein said access provides at least a threshold level of anonymity within records/information retrieved from the defined set of patient records/information based on the user ID and the first role, and wherein the defined set of patient records/information are defined based on the user ID and the first role code of the current user.

2. The method of claim 1, further comprising:
   receiving a second role code associated with a second role of the current user at the interface of the computer database environment; and redefining the defined set of patient records/information to which the current user is allowed access based on the user ID and the second role code.

3. The method of claim 2, wherein the first and second roles of the current user are associated with a single patient.

4. The method of claim 3, wherein the single patient is a member of a medical study, the method further comprising: obscuring data associated with other members of the medical study to provide a level of anonymity to the other members of the study.

5. The method of claim 2, further comprising generating a report associated with the current user, the report summarizing patient records/information accessed by the current user.

6. The method of claim 5, further comprising providing the generated report to at least one state government official, federal government official and/or local institution official.

7. The method of claim 1, further comprising: receiving a request for patient records/information in the defined set of patient records/information at the interface of the computer database environment; determining if results of the received request meet a threshold level of anonymity responsive to the received request; and providing access to the results of the received request if it is determined that the threshold level of anonymity has been met.

8. The method of claim 7, further comprising denying access to the results of the received request if it is determined that the threshold level of anonymity has not been met.

9. The method of claim 7, further comprising:
modifying the results of the received request so that the modified results meet the threshold level of anonymity if it is determined that the threshold level has not been met; and
providing access to the modified results.

10. The method of claim 1, wherein allowing access further comprises allowing access to the defined set of patient records/information based at least one access rule defined by at least one state government official, federal government official and/or local institution official.

11. A system for providing a level of anonymity to patient records/information, the system comprising:
a processor;
a database communicatively connected to the processor and having stored thereon a defined set of patient records/information;
one or more user interface devices;
program instructions executing on the processor to enable the processor to access the database and provide a computer database environment, which is accessible via the one or more user interface devices, wherein the program instructions when executed by the processor are configured to:
receive a unique user identification (ID) associated with a current user at an interface of the computer database environment;
receive a first role code associated with a first role of the current user at the interface of the computer database environment; and
allow access to the defined set of patient records/information in the computer database environment, wherein said access provides at least a threshold level of anonymity within records/information retrieved from the defined set of patient records/information based on the user ID and the first role, and wherein the defined set of patient records/information are defined based on the user ID and the first role code of the current user.

12. The system of claim 11, wherein the program instructions executing within the computer database environment are further configured to:
receive a second role code associated with a second role of the current user at the interface of the computer database environment; and
redefine the defined set of patient records/information to which the current user is allowed access based on the user ID and the second role code.

13. The system of claim 12, wherein the first and second roles of the current user are associated with a single patient.

14. The system of claim 13, wherein the single patient is a member of a medical study, the program instructions executing within the computer database environment being further configured to: obscure data associated with other members of the medical study to provide a level of anonymity to the other members of the study.

15. The system of claim 12, wherein the program instructions executing within the computer database environment are further configured to generate a report associated with the current user, the report summarizing patient records/information accessed by the current user.

16. The system claim 15, wherein the program instructions executing within the computer database environment are further configured to provide the generated report to at least one state government official, federal government official and/or local institution official.

17. The computer program product of claim 12, wherein the first and second roles of the current user are associated with a single patient.

18. The computer program product of claim 17, wherein the single patient is a member of a medical study, the computer program product further comprising:
computer readable program code configured to obscure data associated with other members of the medical study to provide a level of anonymity to the other members of the study.

19. The system of claim 11, wherein the program instructions executing within the computer database environment are further configured to:
receive a request for patient records/information in the defined set of patient records/information at the interface of the computer database environment;
determine if results of the received request meet a threshold level of anonymity responsive to the received request; and
provide access to the results of the received request if it is determined that the threshold level of anonymity has been met.

20. The system of claim 19, further wherein the program instructions executing within the computer database environment are further configured to deny access to the results of the received request if it is determined that the threshold level of anonymity has not been met.

21. The system of claim 19, wherein the program instructions executing within the computer database environment are further configured to:
modify the results of the received request so that the modified results meet the threshold level of anonymity if it is determined that the threshold level has not been met; and
provide access to the modified results.

22. The system of claim 11, wherein the program instructions executing within the computer database environment are further configured to allow access to the defined set of patient records/information based at least one access rule defined by at least one state government official, federal government official and/or local institution official.

23. A computer program product for providing a level of anonymity to patient records/information, the computer program product comprising:
computer readable storage medium having computer readable program code embodied in said medium, the computer readable program code comprising:
computer readable program code configured to receive a unique user identification (ID) associated with a current user at an interface of a computer database environment;
computer readable program code configured to receive a first role code associated with a first role of the current user at the interface of the computer database environment; and
computer readable program code configured to allow access to a defined set of patient records/information in the computer database environment, wherein said access provides at least a threshold level of anonymity within records/information retrieved from the defined set of patient records/information based on the user ID and the first role, and wherein the defined set of patient records/information are defined based on the user ID and the first role code of the current user.

24. The computer program product of claim 23, further comprising:
   computer readable program code configured to receive a second role code associated with a second role of the current user at the interface of the computer database environment; and
   computer readable program code configured to redefine the defined set of patient records/information to which the current user is allowed access based on the user ID and the second role code.

25. The computer program product of claim 24, further comprising computer readable program code configured to generate a report associated with the current user, the report summarizing patient records/information accessed by the current user.

26. The computer program product of claim 25, further comprising computer readable program code configured to provide the generated report to at least one state government official, federal government official and/or local institution official.

27. The computer program product of claim 23, further comprising:
   computer readable program code configured to receive a request for patient records/information in the defined set of patient records/information at the interface of the computer database environment;
   computer readable program code configured to determine if results of the received request meet a threshold level of anonymity responsive to the received request; and
   computer readable program code configured to provide access to the results of the received request if it is determined that the threshold level of anonymity has been met.

28. The computer program product of claim 27, further comprising computer readable program code configured to deny access to the results of the received request if it is determined that the threshold level of anonymity has not been met.

29. The computer program product of claim 27, further comprising: computer readable program code configured to modify the results of the received request so that the modified results meet the threshold level of anonymity if it is determined that the threshold level has not been met; and
   computer readable program code configured to provide access to the modified results.

30. The computer program product of claim 23, wherein the computer readable program code configured to allow access further comprises computer readable program code configured to allow access to the defined set of patient records/information based at least one access rule defined by at least one state government official, federal government official and/or local institution official.

\* \* \* \* \*